US011141087B2

(12) United States Patent
Aiyer

(10) Patent No.: US 11,141,087 B2
(45) Date of Patent: Oct. 12, 2021

(54) OPTICAL DEVICE FOR NON-INVASIVE CONTINUOUS MONITORING OF BLOOD GLUCOSE LEVEL AND HBA1C CONCENTRATION

(71) Applicant: Arun Ananth Aiyer, Fremont, CA (US)

(72) Inventor: Arun Ananth Aiyer, Fremont, CA (US)

(73) Assignee: Arun Ananth Aiyer, Fremont, CA (US)

( * ) Notice: Subject to any disclaimer, the term of this patent is extended or adjusted under 35 U.S.C. 154(b) by 0 days.

(21) Appl. No.: 16/849,233

(22) Filed: Apr. 15, 2020

(65) Prior Publication Data

US 2020/0359939 A1     Nov. 19, 2020

Related U.S. Application Data

(60) Provisional application No. 62/849,279, filed on May 17, 2019.

(51) Int. Cl.
| | | |
|---|---|---|
| *A61B 5/1455* | (2006.01) | |
| *A61B 5/145* | (2006.01) | |
| *A61B 5/1495* | (2006.01) | |
| *A61B 5/00* | (2006.01) | |

(52) U.S. Cl.
CPC .......... *A61B 5/1455* (2013.01); *A61B 5/1495* (2013.01); *A61B 5/14532* (2013.01); *A61B 5/14546* (2013.01); *A61B 5/7246* (2013.01); *A61B 2562/0238* (2013.01)

(58) Field of Classification Search
None
See application file for complete search history.

(56) References Cited

U.S. PATENT DOCUMENTS

2004/0199060 A1\* 10/2004 Oshima ................ A61B 5/1455
600/310

\* cited by examiner

*Primary Examiner* — Eric F Winakur
*Assistant Examiner* — Marjan Fardanesh
(74) *Attorney, Agent, or Firm* — Geeta Kadambi; Riddhi IP LLC

(57) ABSTRACT

A sensor device which is adapted for detecting target molecules in-vitro and in-vivo, comprises a MIR source for exciting the target species and a probe beam with split frequency to measure the effect of excitation. The latter uses a heterodyne interferometer operating at a beat frequency ~ KHz. to MHz. The photo-thermal excitation of target species leads to refractive index change. The RI change produces probe beam displacement and is measured using a 1) grating heterodyne interferometer, 2) grating deflection amplifier and 3) evanescent field heterodyne interferometer. The measured RI change can be related to specie concentration change in target volume. Furthermore, a sensing method for detecting HbA1c concentration and its change with thermal excitation is described in terms of phase shift of the OCT spectrum obtained with spectral domain optical coherence tomography (SD-OCT).

12 Claims, 6 Drawing Sheets

Source: Sensors, vol.16, p 1663, 2016

Reference and Phase-shifted Beat signal from the probe beam

Wire grid polarizer (WGP) and grating element (GE) integrated to the base surface of total internal reflection element

OPTICAL DEVICE FOR NON-INVASIVE CONTINUOUS MONITORING OF BLOOD GLUCOSE LEVEL AND HBA1C CONCENTRATION

CROSS-REFERENCE TO RELATED APPLICATIONS

This application claims the benefit of U.S. Provisional Patent Application No. 62/849,279 filed May 17, 2019 by the present inventor, which is incorporated herein by reference in its entirety.

STATEMENT REGARDING FEDERALLY SPONSORED RESEARCH OR DEVELOPMENT

Not applicable

REFERENCE TO A SEQUENCE LISTING, A TABLE, OR A COMPUTER PROGRAM LISTING COMPACT DISC APPENDIX

Not applicable

FIELD OF THE INVENTION

The present invention relates to the field of medical devices and in particular to the monitoring of blood glucose and HbA1c level and their variations using non-invasive method

BACKGROUND OF THE INVENTION

Diabetes mellitus (DM), or diabetes, is a serious metabolic disease characterized by chronic elevation of blood glucose (i.e., hyperglycemia) resulting from defects in insulin secretion, insulin action, or both. No definitive cure is known at this time. Diabetes is generally categorized into three major types based on etiology: Type 1 diabetes (insulin-dependent diabetes mellitus), Type 2 diabetes (adult onset diabetes mellitus or noninsulin dependent diabetes), and gestational diabetes mellitus. Diabetes is a leading cause of morbidity and mortality and is associated with substantial healthcare and societal costs. Intensive insulin therapy, a term used to describe tight management of blood glucose levels, has been shown to reduce the risk of long-term diabetic complications by lowering average blood sugar levels, but also increases the risk of hypoglycemia, which can result in serious morbidity and even death, and causes fear of hypoglycemia which is a major barrier to optimal glucose control. Real-time continuous glucose monitoring (CGM) is advanced glucose monitoring technology that continuously measures interstitial fluid glucose levels, displays the current blood glucose level as well as the direction and rate of change, and uses alarms and alerts to inform patients when blood glucose is exceeding or falling below specified thresholds. Conventional fingerstick self-monitoring of blood glucose (SMBG), sometimes called intermittent monitoring, is a technique for testing blood glucose using a portable glucose meter designed for home use. SMBG provides an instantaneous reading of current blood glucose levels at single points in time but cannot indicate whether the glucose level is on its way up or down. CGMs were designed to aid in the detection of episodes of hyperglycemia and hypoglycemia, facilitating both acute and long-term therapy adjustments, which may minimize these excursions. CGMs can be used as stand-alone devices or in conjunction with compatible insulin pumps [14].

PRIOR ART

Several optical techniques are being investigated for non-invasive blood glucose measurement [1,2]. Of the several optical techniques, photo induced thermal (PIT) effect induced by the absorption of mid-IR (MIR) radiation by biological tissues has been utilized in medical devices. PIT induced acoustic wave detection, PIT spatial heterodyne imaging PIT radiometry, and PIT deflectometry are some of the approaches used in detecting the response of biological samples to PIT phenomenon [3-10]. Of these three approaches, PIT deflectometry is attractive for glucose sensing because of its inherent higher S/N. In prior art, the deflectometer uses position sensing detector (PSD) for recognizing the deflection of the probe beam resulting from thermal lensing created by the absorption of MIR radiation by the sample [46, 47]. The magnitude of deflection is directly related to glucose concentration. The sensitivity of detection is dependent on PSD (segmented or monolithic detector) position resolution and its noise equivalent power (NEP). These parameters will limit the smallest change in glucose concentration that can be detected. Optical coherence tomography (OCT) is a non-invasive optical technique that is used to measure amount of hemoglobin and glycated hemoglobin in samples [11,12,13]. However, all these measurements are done in lab environment and not under in-vivo conditions. No viable approach to monitor change in HbA1c concentration in-vivo has been demonstrated to the best of these inventor's knowledge.

SUMMARY OF THE INVENTION

Methods and apparatus for continuous monitoring of daily blood glucose level change and HbA1c are described in this invention. The measurements are done using photo thermal lensing effect in conjunction with phase grating heterodyne interferometry and Optical Coherence Tomography (OCT) respectively. For glucose monitoring, epidermis layer under the skin is chosen for better target specificity. See FIG. 3. Skin surface, in the chosen part of the body, is irradiated with MIR radiation of appropriate wavelength. Since MIR radiation is absorbed within a depth of about ≤100 µm of the skin surface, glucose molecules, in the Epidermis layer of the skin, absorbs the radiation causing local heating, which results in thermal spiking near the skin surface. Magnitude of spiking depends on heat generated from absorption of MIR which is directly correlated to glucose concentration. Refractive index gradient caused by the spike will lead to formation of thermal lens where the spiking occurs [47]. A probe beam that interacts with the lens is subjected to modification to its propagation direction and phase. Change in propagation direction, further modified by a diffraction grating, manifests as amplified angular deflection of 1-order or higher order diffracted beam. The modified beam deflection could be measured by a Position Sensing Detector (PSD). This measurement is directly proportional to glucose concentration. In this invention, enhancement to detection sensitivity is made of two components. First is geometrical component from beam propagation distance and second component is from a cosine scale factor as discussed in section [0025].

Displacement of the probe beam induced by thermal lensing, leads to a relative displacement between the beam and the diffraction grating. The resulting phase shift experienced by the probe beam could be measured via heterodyne interferometry. The measured phase shift is directly proportional to glucose concentration.

Change in glucose level is further checked by detecting change in glucose refractive index in the Epidermis due to its concentration variance. This is done by having the evanescent field of a s- or p-polarized light probe the sample site. The optical pathlength change (phase shift) experienced by the probe beam, due to index change, is detected via heterodyne interferometry by mixing it with a frequency shifted s- or p-polarized beam. The measured phase shift is directly proportional refractive index change which in turn is directly dependent on glucose concentration.

In a second variant of this evanescent probing, the sample site is pumped by MIR light. MIR light absorbed by glucose molecules in the Epidermis, heats-up the selected site. The resulting change in index can be sensed by the evanescent field of a s- or p-polarized light probe the sample site. The optical pathlength change (phase shift) experienced by the probe beam, due to heat induced index change, is detected via heterodyne interferometry by mixing it with a frequency shifted s- or p-polarized beam. The measured phase shift is directly proportional refractive index change which in turn is directly dependent on glucose concentration. Measurements made with and without MIR pump would track each other with glucose concentration change.

To monitor HbA1c % in vivo, NIR beam centered around 960 to 1060 nm, but not limited to, is used as pump beam. This wavelength is better absorbed by glycated Hemoglobin than by other interfering molecules [15]. However, the amplitude change in absorption spectra may be difficult to monitor especially in vivo. Therefore, SD-OCT technique is used for monitoring change in HbA1c concentration. Using SLED in 700-800 nm spectral region or another appropriate spectral region, SD-OCT fringe pattern of the sample is recorded in vivo. The fringe pattern is Fourier transformed in k-space and the phase of the signal is determined using the real and imaginary parts of Fourier spectrum. This approach is at least an order to three orders of magnitude more sensitive than what is achievable in optical depth domain. Even though HbA1c monitoring, using this invention, can be done where non-invasive access to hemoglobin is possible, venous blood is preferred since free glucose molecules, deoxy-Hemoglobin and water molecules present in there have lower absorbance at around 970 nm [16,17,18,19].

SD-OCT probing of venous blood could be implemented using 700-800 nm NIR light with narrow band 970 nm as pump source. The reflected light is analyzed using either a CCD array spectrometer having a pixel bandwidth that corresponds to temporal coherence ≤2× depth at which HbA1c needs to be monitored or a monolithic photo diode detector system. In the spectrometer approach, recorded fringe pattern will be analyzed using FFT or Hilbert transform technique to extract signal phase information that is related to HbA1c concentration and changes in its level. From fringe data, vein wall thickness and vein lumen diameter can also be determined. One can also use model-based algorithms to extract the same information. In the latter approach, the substrate is modeled as a film stack made up of multiple layers each one with its own unique material composition.

BRIEF DESCRIPTION OF THE DRAWINGS

Further details and advantages of the invention are described in the following with reference to the attached drawings, which show in:

FIG. 5 is a schematic representation of an alternate and integrated implementation of the elements 34, 40 and 41 shown in FIG. 1a.

DETAILED DESCRIPTION OF PREFERRED EMBODIMENTS

In the rendition given below, certain examples are given to illustrate many implementations and uses of the device and to explain specific details of the invention. Given the benefit of this disclosure, a person of ordinary skill in the art can put the invention into practice. Unless otherwise clear from the context, like numerals refer to similar structures in different figures. Moreover, those skilled in the art will acknowledge that embodiments described below may be executed in a multiplicity of ways. For example, the generation and detection of photo-thermal sites could be achieved with guided wave propagation or with free space propagation from incoherent source instead of laser beams as shown in figures. Thus, through this disclosure we intend to include all possible execution of the invention.

All embodiments of the present invention incorporate apparatus and methods for a robust sensor capable of speed, accuracy, sensitivity, robustness and device reusability. Details of optical phase shift effected by relative motion between a grating and an incident beam, details of measuring phase shift of the heterodyne signal, and details of measuring phase variation of SD-OCT signal for HbA1c concentration are not described as such, as they are known from prior art [20-23, 24, 25,26].

Sensor Device for Non-Invasive CGM

Figure 1A:
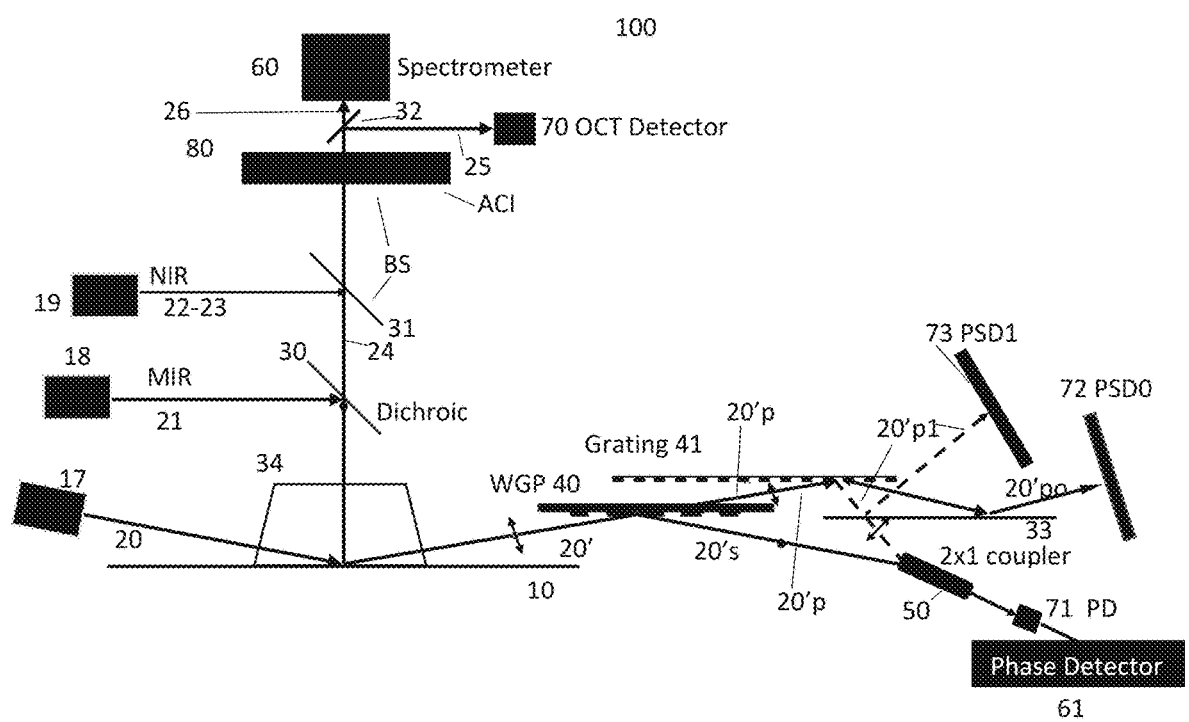
FIG. 1a is a schematic illustration of a sensor device according to an embodiment of the invention.

Referring to Fig 1a, a schematic diagram of an exemplary Continuous Glucose Monitoring (CGM) and Continuous HbA1c Monitoring (CAM) device 100 is shown. It consists of a first mid infrared light source 18 and beam 21, dichroic mirror 30, Total Internal Reflection Element (TIRE) 34, Probe source 17 that is a heterodyne laser and beam 20, Wire Grid Polarizer (WGP) 40, grating element (GE) 41, beam splitter 33, Position Sensing Detector (PSD) 72 and 73, Photo Detector (PD) 71, Phase Detection electronics 61 also referred to as phasemeter or phase detector, a second NIR source 19 with pump beam 23 centered around 960 to 1060 nm but not limited to, NIR probe beam 22 in 700-800 nm spectral region with returning probe beams 25 and 26, beam splitters (BS) 31 and 32, auto-correlation interferometer (ACI) 80, spectrometer 60 and OCT detector 70.

Figure 1B:
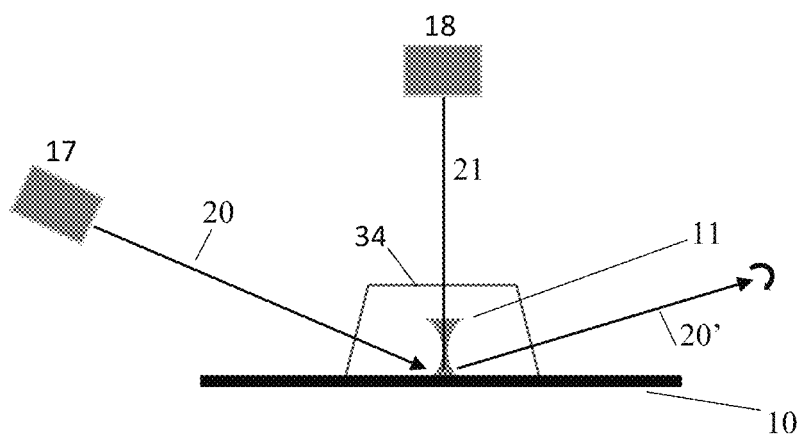
FIG. 1b is a schematic illustration of evanescent mode excitation of target site and probe beam interrogation in the embodiment.

A Quantum Cascade Laser (QCL) 18 operating in mid infrared spectral range provides beam 21 that is absorbed by Glucose molecules. The beam may consist of one or a bundle of wavelengths in the 2μ to 10μ. Assuming a gaussian beam profile, the thermal profile created from absorption should have a similar profile. This means that the thermal lens will have a concave lens characteristic shown as 11 in Fig 1b [47]. The probe beam 20, entering total internal reflecting element 34, interacting with this lens 11 will cause refraction of beam 20' which induces displacement of beam 20' that is significantly different from displacement in normal total internal reflection. The power of the lens will depend directly on the incident mid infrared laser power and the number of absorbing molecules present in the pump/probe volume. Pump-probe laser beams are aligned to have total overlap at the TIRE to maximize probe beam deflection. The probe beam is composed of two orthogonally polarized EM waves with frequency difference of the order a of a few KHz. to MHz. After interacting with the thermal lens, the probe beam passing through a WGP 40, has its s-polarization 20's reflected by the WGP 40, while the p-polarized light passes through. The transmitted light undergoes diffraction at grating element 41. The 0- and 1-order or higher order diffracted beams are further split at beam splitter 33. The reflected beams 20'p1 and 20'p0 are monitored using PSDs 72. The transmitted 20'p1 is mixed with 20's via a PM fiber optic coupler 50. The beat signal generated by mixing the two polarizations is detected by PD 71 and sent to phase detection electronics 61. When the thermal lens induced beam bending occurs, beam 20'p undergoes displacement over 41. The relative motion between 41 and 20'p introduces a phase shift $\Delta\phi$ in beam 20'p1.

$$\Delta\phi = \frac{2\pi}{\lambda} \times \left(\Delta x \frac{m\lambda}{d}\right) \quad (1)$$

where $\Delta x$ is the relative displacement between 41 and 20'p, d is the grating pitch and m is the diffraction order, equal to 1, 2 or 3 in this embodiment [44,45]. Higher order diffraction can also be used.

Figure 4:
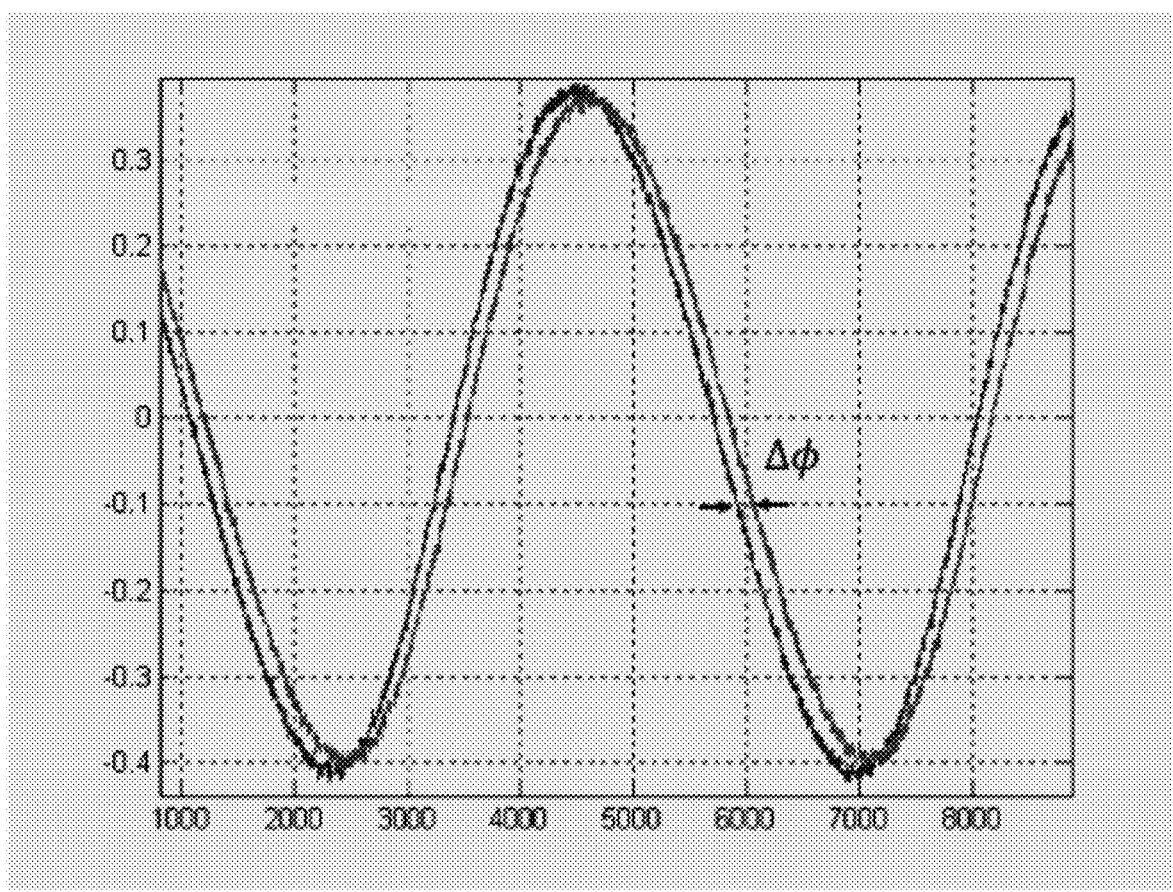
FIG. 4 is a graphical illustration of phase shifted signals in a heterodyne interferometer.

To measure $\Delta\phi$, 20'p1 is mixed with 20's and the phase of the signal is computed using either Fourier transform, or Hilbert transform technique. The phase shift is measured with respect to a reference. This reference can be an internally generated sine wave, or a signal gotten by mixing 20's and 20'p0 (mixing not shown in the FIG. 1a). See FIG. 4. With this approach, maximum phase shift of $2\pi$ that can be detected will be $\Delta x = d/m$. A sensitivity of the order of a few micro radians can be achieved with commercially available phasemeter. The beam displacement $\Delta x$ is dependent on amount of heating that occurs in the TIRE, which in turn depends on the concentration of absorbing Glucose molecules in the irradiated sample volume. Therefore, the magnitude of $\Delta x$ can be controlled and potentially kept under d/m by controlling the output power of MIR source.

Prior art uses TIRE 34 deflected beam and monitors it using PSDs. In this invention, PSD data is used to monitor relative displacements >d/m, thereby extending the dynamic range of the sensor without losing sensitivity. Additionally, phase noise due to 20'p beam wander can be subtracted out by measuring the wander of 20'p0 and 20'p1 in 72 and 73. This helps to reduce phase error and enhance S/N.

In the second embodiment, the angular deflection of the diffracted beam 20'p1 is detected by its displacement on PSD 73. Refer to FIG. 1a. For a deflection angle change of $d\alpha$, diffracted beam displacement is $$D1 = 2 \times d\alpha \times L_1 + \times 2 \times d\alpha \times L_2 \times \left(\frac{\cos\alpha}{\cos\theta}\right) \quad (2)$$

$$D0 = 2 \times d\alpha \times L \quad (3)$$

where D1 is the total displacement of diffracted beam on 73, D0 is the displacement of 0-order beam on 72 and L is the beam throw (path length) from TIRE 34 to PSD 72, $L_1$ is the beam path from 34 to grating 41 and $L_2$ is beam path from 41 to 73. By choosing a grating configuration in which the diffraction angle $\theta$ is engineered to be $\alpha \ll \theta < \pi/2$, the measurement sensitivity of the second embodiment can be enhanced by the scaling factor $$\left(\frac{\cos\alpha}{\cos\theta}\right)$$

[48].

Figure 2:
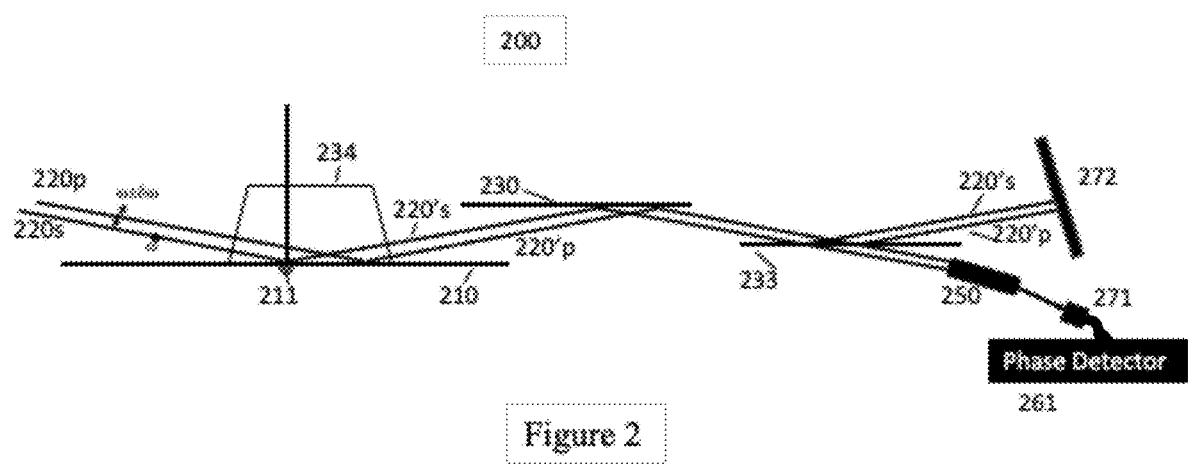
FIG. 2 is a schematic illustration of a sensor device per a third embodiment of the invention.
Figure 3:
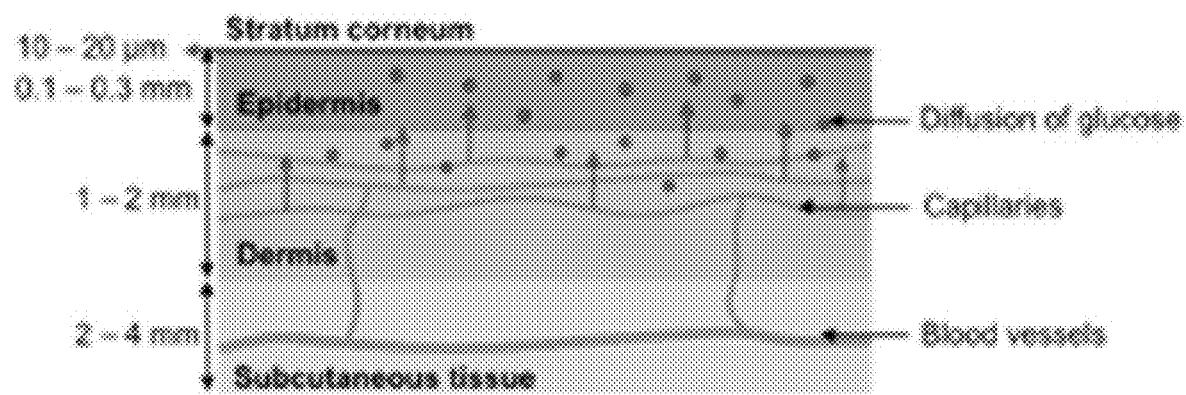
FIG. 3 is a schematic illustration of cross-section of skin.

In a third embodiment of the sensor, the probe beams with s- and p-polarizations are spatially separated, as they enter the total internal reflection element 234, as shown in FIG. 2. The probe beam either 220s- or 220p-polarized, interrogates the area irradiated with mid infrared light beam 221. As in the previous embodiment, the pump 221 and probe beams have exact overlap or some degree of overlap. The frequency difference between p- and s-polarizations is ~ a few KHz. to MHz. The polarization not overlapped with the mid infrared beam is incident on an adjacent spot that is separated enough not to experience the thermal profile induced by the mid infrared light. In this embodiment, the total internally reflected polarization beams 220'p and 220's experiences phase change introduced by refractive index differential in the evanescent region 211 in sample 210. This index differential is a function of glucose level change. Additionally, the differential introduced by mid infrared absorption is also a function of Glucose level in the epidermis. Thus, the measurements taken with and without mid infrared pump should track each other linearly. In the third embodiment, the spatially separated polarizations are mixed via coupler 250 after being steered by optical element 230 and transmitted by optical element 233. The phase shift due to optical path length change is detected via photodetector 271 and phasemeter 261 electronics. The phasemeter is also referred to as phase detector or phase detection electronics. The phase shift is measured with respect to a reference. This reference can be an internally generated sine wave.

In fourth embodiment, the deflection of polarized probe beam can be measured using PSD 272. The advantage of this embodiment is that one of the spatially displaced light 220p or 220s that does not overlap with mid infrared beam spot on the sample will act as the reference signal. See FIG. 2. The distance between the reference and measurement beams 220'p and 220's on position sensing detector 272 will be independent of noise because of its near common-path beam configuration.

In a fifth embodiment of the sensor (not shown schematically here) the probe beam consists of coaxially located s- and p-polarizations with frequencies $\omega$ and $\omega \pm \delta\omega$ respectively. The shift frequency $\delta\omega$ is ~ of a few KHz. to MHz. Both polarizations experience differential penetration depth and phase change due to index change resulting from Glucose concentration change in the evanescent region [27, 43]. Thus, measure of phase differential would be a direct measure of Glucose concentration and its change thereof. As in the third embodiment, the two beams are mixed via coupler similar to 250 or by using a polarizer analyzer and phase shift due to optical path length change is detected via electronics similar to 271 and 261. The phase shift is measured with respect to a reference. This reference can be an internally generated sine wave.

Figure 5:
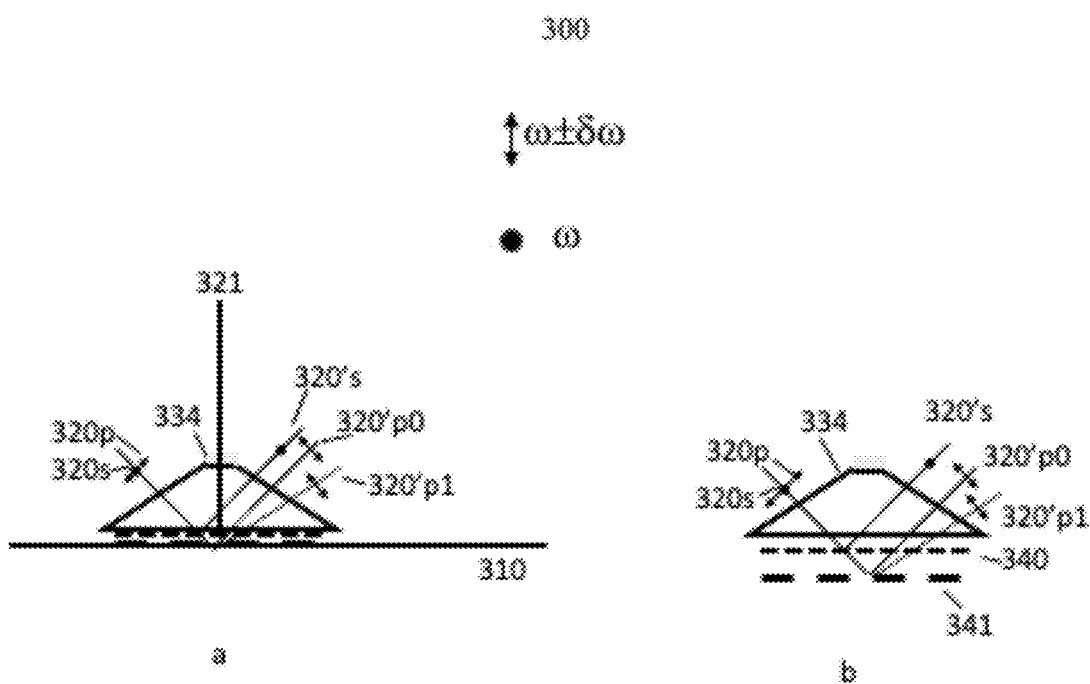

In a sixth embodiment of the invention, WGP and grating are integrated on to the base surface of the TIRE 334 as shown in FIG. 5a and (exploded view in FIG. 5b). As shown in there, WGP 340 and the grating 341 are kept in close proximity to the base surface of 334 and in that order. The former separates the polarizations while the latter diffracts the transmitted polarization. The spacing between 340 and 341 is variable and can vary from zero to a maximum value. The medium between 340 and 341 can be any that transmits pump beam 321 and probe beam consisting of p-polarization 320p and s-polarization 320s. This Integrated TIRE (ITIRE) could be positioned on or in close proximity to, the sample 310. The thermal lensing caused in 310 by mid infrared beam 321 could lead to displacement of 341 in both vertical and lateral (perpendicular to groove) directions. This introduces relative motions between gratings and beam 320p/320s that could induce a phase shift in $320'p1$. The magnitude of the phase shift would be proportional to glucose concentration. The phase measurement approach would be the same as what is described in sections [0022] and [0023]. Sensitivity of deflectometer that uses PSD detection would nominally depend on pathlength of deflected beam among other things. Longer beam throw could lead to an increase in sensor form (envelope) factor and or could make the aft optics more complex. Deflectometer that uses relative beam displacement on grating can detect smaller beam deflection(s) since the beam sees a phase shift of $2\pi$ for beam movement equal to grating pitch. Hence the beam throw could be smaller resulting in reduced sensor form factor.

Pathlength change experienced by $320'p0$ as a result of the vertical displacement of 341 induced by thermal spike caused by photo-thermal excitation of glucose molecules can be measured by mixing $320's$ and $320'p0$ (similar to thin film reflectance phenomenon). The magnitude of the phase shift, corresponding to the pathlength change, would be proportional to glucose concentration. The phase measurement approach would be the same as what is described in sections [0022] and [0023].

In a seventh embodiment of the CGM sensor, only the WGP is integrated to the base surface of the ITIRE. This embodiment, though not shown in a schematic, could be explained with the help of FIG. 5 and FIG. 2. In this configuration, the s-polarization will be reflected by WGP and the transmitted p-polarization will probe the evanescent region in the sample similar to 211 in FIG. 2. For an included mid infrared pump beam intensity, the optical phase shift experienced by the probe beam undergoing total internal reflection (TIR) would track glucose concentration in the sample. This is so, since the phase shift experienced by the beam is dependent on the RI of the rarer medium 211 in sample 210 [43]. The phase measurement approach would be the same as what is described in sections [0022] and [0023] but not limited to it.

The CGM capability of embodiments described above provides for daily averaged glucose (DAG) values. Since there is a linear relationship between DAG and HbA1c concentration, this invention delivers a method to calculate, on a regular basis, % HbA1c in patients [41,42]. Ref [42] establishes this relation as $$DAG (mg/dl) = 28.7 \times A_{1c} - 46.7 \quad (4)$$

with a correlation coefficient $R^2=84\%$ over a 3-month study. With the CGM invention reported here, which has the ability to detect smaller glucose variation, HbA1c trend over a shorter period of time could be monitored.

Sensor Device for Non-Invasive Hba1C Monitoring

HbA1c is defined as hemoglobin A with glucose attached to the NH2-terminus valine of one or both β-chains. The ratio of glycated hemoglobin to total hemoglobin, usually given as %, is a measure of the prior diabetic control of a patient. The ratio 4 to 6% is considered to be non-diabetic and all values >6%, depending what that value is, is classified as pre-diabetic, type I diabetic, type II diabetic etc. Currently, % HbA1c is determined from blood draws. The % change in HbA1c, as measured by current method, is noticeable only over a three-month period and not sensitive enough to measure small changes in HbA1c concentration occurring over a shorter time period.

A Spectral Domain Optical Coherence Tomography (SD-OCT) sensor in the exemplary embodiment shown in FIG. 1a shall monitor HbA1c in-vivo on a daily basis. This SD-OCT sensor can be configured with all the CGM embodiments described above or can be used as a stand-alone sensor. The purpose of SD-OCT is to measure change in refractive index as the concentration of HbA1c changes [30]. In order to monitor smaller variations in HbA1c concentration, we shall calculate phase of SD-OCT signal and its variation thereof by analyzing the spectrometer 60 data employing either Fourier transform, or Hilbert transform technique [33,34] Additionally, unlike prior art, SD-OCT signal measurements shall be taken with and without thermal excitation of glycated Hb molecules.

The SD-OCT sensor used in this invention has NIR pump source and a broadband source in the 700 nm to 800 nm spectral range represented by 19. The pump source operating at wavelength centered around 960 to 1060 nm, but not limited to that range. See FIG. 1a. NIR pump radiation represented by 23 and 24 is chosen to thermally excite glycated hemoglobin molecules as it shows slightly better absorption at this wavelength than free glucose, water and oxy/de-oxy hemoglobin molecules, the other major components in the venous blood [28,29,32]. In-vivo measurement of HbA1c shall be taken in venous blood as its oxygen saturation is 25 percent less than that of arterial blood. Glycated oxy-hemoglobin molecules can also be found in venous blood and they do not give up their oxygen to any tissues. Ref [28] shows that glycated hemoglobin exhibits higher affinity to oxygen. Glycated hemoglobin & glycated oxy-hemoglobin molecules absorb more radiation at wavelengths on either side of 970 nm center than does deoxy-hemoglobin [29]. A study reported in ref [31] points to the fact that glycated hemoglobin has more ability to bind water due to water-glucose interactions that tends to decrease free water in the sample and, thereafter, decrease overall water absorbance. This, in conjunction with the study reported in ref [15] means that discriminatory heating glycated hemoglobin can be achieved with pump beam in the spectral vicinity of 970 nm, but not limited to it.

The phase measurements that correspond to HbA1c concentration change and that due to photo-thermally induced $dc_{A1c}/dT$ change should track each other. Such correspondence means that the measurements are HbA1c specific.

To monitor HbA1c change, start acquiring normalized SD-OCT spectral data with the broadband beam 22 from source 19 and spectrometer 60 sensing return beam 26 and OCT detector 70 sensing beam 25, repeatedly for a week. Normalize the spectrum with pump beam on with the spectrum taken without the pump. From these, an averaged data set that can be used as reference data is generated. The same thing is repeated every week for the next few months to generate a super set of reference data. Each week or a chosen time period, SD-OCT data taken during the week is averaged and is normalized to reference data to mitigate effect of noise sources such as blood vessel diameter fluctuations, body part motions, influence of blood components that vary day to day but are not related to Hb glycation and other random noise signals. Thus, each normalized spectrum has embedded in it, information regarding on-going Hb glycation reactions and subsequent HbA1c concentration change from the previous week(s). Initially this data set may have some scatter. Linear fit to the data could provide trend information. Non-linear fit would provide information on swings trends. In case of patients with advanced diabetes, trend information could be made available to care givers on a regular basis for more robust diabetes status analyses and timely pertinent treatment.

Reference data could also be generated by averaging data from more than one week. Change in the spectral signature/behavior of later collected data when normalized to reference generated using earlier timeline data could be a bio marker for % HbA1c change.

To achieve in-vivo measurement of HbA1c concentration, in-vitro baseline measurements for calibrations need to be done ahead. This could be generally achieved using sample solutions containing known proportion of blood constituents such as Glucose, Hb, HbA1c and other relevant components in vein sized polymer tubes. Knowing the tube inner diameter, refractive index (RI) of the fluid inside the tube can be determined from SD-OCT measurements. The refractive index change as a function of A1c concentration could be determined from $$n = n_0 + \alpha C \tag{5}$$

where $n_0$ is the refractive index of the solvent, $\alpha$ is the specific refraction increment and C is the concentration [35,34]. If the subsequent measurements are made on sample with only concentration change, then the new refractive index value could be represented by $$n_{new} = n_{old} + \alpha \Delta C \tag{6}$$

where $n_{old}$ previously measured refractive index represented by eqn (5).

Baseline concentration could also be determined by obtaining SD-OCT signals in A-scan mode [40]. The measured signal dependence on sample thickness is given by $$-\ln\left(\frac{I(d)}{I_0}\right) = \mu_a \times d - \ln(R) \tag{7}$$

where I(d) is signal returning from depth d, $\mu_a$ is the absorption coefficient per cm., R is the ratio of return signal to incident signal. Slope of eqn (7) gives absorption coefficient which in turn is proportional to concentration [38,39]. For smaller phase shifts, phase measurement in conjunction with eqn (5) and eqn (6) could be preferable while eqn (7) would be more applicable to larger attenuation variances.

Both OCT amplitude and phase signals would be measured with and without the NIR pump beam. If these measurements correspond to HbA1c index change due to concentration change and index change induced by the photo-thermal effect of the pump, then the Δs in these two measurements could track each other. Such correspondence means that the measurements are HbA1c % change specific.

This invention further allows for validating % HbA1c obtained from DAG measurement with that from SD-OCT measurement.

The ability to measure CGM with a sensor that includes different techniques, would provide a higher degree of confidence in the measurements while enhancing their accuracy with smaller standard deviations.

The procedure for measuring glucose concentration (CGM) includes but not limited to the following steps, procedure and methodology.

Using the CGM sensor described in the above-mentioned embodiments or combination thereof, measure solutions with different glucose concentration and establish an appropriate relationship between sensor data and concentration. This includes sensor calibration and biasing. Produce look up table (LUT) for an included range of glucose concentration. LUTs could be generated for a range of MIR laser power as well.

Repeat the above steps with human blood in-vitro, with differing glucose concentration, obtained from volunteers. Also, determine blood glucose concentration using standard blood work methodology.

Establish correlation between the two data sets. This would include additional calibration and biasing considerations.

From the measurement data sets obtained with glucose solution sample and human blood, establish relevant scaling and biasing parameters that could be used in sensor calibration. This approach should thus provide for a calibration procedure without having to draw blood.

During in-vivo measurements, sensor data taken with different pump powers could be compared to the in-vitro LUTs generated with glucose solutions and blood samples to determine correspondence between the two measurement modalities. Adjust scaling and bias parameters to obtain higher degree of correlation between in-vivo and in-vitro measurements.

Procedure for measuring HbA1c includes, but not limited to, the following steps, procedures and methodology.

Using CGM data taken over an extended period of time, % HbA1c could be predicted using the relationship similar to that in eqn (4) but not limited only to it.

At the end of the same extended period, measure % HbA1c using the standard blood work method.

Working with a few samples, determine correlation between predicted data and blood-work data. Establish scaling and biasing factors as need to tune eqn (4) to improve correlation. Predictive A1c value gotten from the improved eqn (4) could be used as the base value for HbA1c measurement using the sensor embodiment and measurement methodology described earlier in sections [0033] through [0041]. This could be used as baseline HbA1c value at the start of CAM measurements.

After the baseline HbA1c % is gotten, measure RI of venous blood both in-vitro and in-vivo. Let us call this ($n_{old}$). Establish required scaling and biasing parameters for higher correlation between the two modes of measurement. Better correlation helps to further validate the in-vivo measurements in commercialized sensor. Next take in-vivo RI measurement(s) at a later date when the A1c concentration could have changed. The new index value could be described by eqn (6) from which the new HbA1c concentration could be determined.

Both Glucose and HbA1c measurements could be taken with and without thermal or other forms of excitation of the relevant molecules. The excitation source could be outside of the sensor envelope or could be part of the sensor envelope or divided between the two modalities in a manner appropriate for product development.

This invention is not limited to only those embodiments and measurement methodologies described here. It is the intent of the inventor to include in this invention other embodiments (optical configurations), measurement steps, methodologies, approaches that could be thought of by those ordinarily skilled in the art. What is described here represents the spirit of the invention and is not intended to limit the scope of its implementation.

The previous examples and embodiments are representative examples of the spirit of the present invention and should not be construed as limiting the scope of the invention. Furthermore, any improvements, enhancements, different physical implementation, different operation sequence, combinations thereof and equivalent counterparts that could be thought of after examining the drawings and understanding the specifications are within the true spirit and scope of the present invention.

Terms used in this disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," the term "could be" or 'would be" should be interpreted as "could be or would be, but not limited to" etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description of embodiments, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited in this disclosure are intended for pedagogical objects to aid the reader in understanding the invention and the concepts contributed by the inventor to furthering the art and are to be construed as being without limitation to such specifically recited examples and conditions. Although embodiments of the present disclosure have been described in detail, it should be understood that, various changes, substitutions, and alterations could be made hereto without departing from the spirit and scope of the present disclosure.

What is claimed:

1. A sensor device for in-vivo use and continuous monitoring of a glucose concentration and a glycated hemoglobin concentration, comprising:
   a total internal reflection element comprising of a top surface, four side surfaces and a bottom or a base surface and is configured to be placed on a skin of a subject to monitor the glucose concentration and the glycated hemoglobin concentration;
   a first near infrared light source is configured to emit a first laser beam at a near-infrared spectral region that encompasses absorption region of a glycated hemoglobin;
   the first near infrared light source is further configured to emit a broadband first probe beam at the near-infrared spectral region selected to measure the glycated hemoglobin in the venous blood, wherein the first laser beam and the broadband probe beam are positioned to be conveyed under the skin through the total internal reflection element;
   a spectrometer and an Optical coherence tomography detector are configured to detect, and analyze a returning reflected broadband probe beam resulting from the probe beam using at least one of a fast Fourier transform and a Hilbert transform of a spectral signal to report a fringe pattern indicating change in the glycated hemoglobin concentration in the venous blood;
   a second mid-infrared laser source including a quantum cascade laser is configured to emit a mid-infrared region laser beam in a spectral region that encompasses an absorption band of the glucose and is positioned to enter the total internal reflection element;
   a heterodyne probe laser system that is configured to emit a second probe beam in a predetermined polarization state is positioned to be conveyed through the total internal reflection element and exit after being reflected by the base surface of the total internal reflection element;
   a wire grid polarizer configured to receive the second probe beam reflected by the total internal reflection element and reflect one predetermined polarization state and transmit another predetermined polarization state;
   a phase detector configured to convert the second probe beam from the heterodyne probe laser system into an electric beat signal and read the phase of the electric beat signal as one measure of the glucose concentration in the interstitial fluid;
   a grating element configured to receive the transmitted predetermined polarization state of the second probe beam and diffract that beam, wherein the diffracted beam undergoes phase shift, when a relative displacement occurs between the diffraction element and the received diffracted second probe beam; and
   a position sensing detector configured to detect and measure change in position displacement of the diffracted second probe beam as a second measure of the glucose concentration in the interstitial fluid.

2. The sensor of claim 1, wherein the second probe beam has a characteristic orthogonally polarized component with frequency difference varying from KHz to MHz.

3. The sensor device of claim 1, wherein the second source laser is a quantum cascade laser source that is used for generating the mid-infrared region laser beam and is absorbed by a glucose molecule resulting in the generation of a thermal lens in the total internal reflection element.

4. The sensor device of claim 3, wherein the mid-infrared region laser beam consists of one or more wavelengths in a 2 μm to 10 μm range.

5. The sensor device of claim 1,
wherein the second probe beam with s-polarization and p-polarization is received by the wire grid polarizer after being reflected by the total internal reflection element after interacting with a thermal lens situated in the total internal reflection element.

6. The sensor device of claim 5, wherein the wire grid polarizer reflects the s-polarization probe beam and transmits the p-polarization probe beam that is diffracted by the grating element.

7. The sensor of claim 6, further comprising of:
a beam splitter is configured to receive a diffracted zeroth order and first order of the p-polarized probe beams and to split the beams further into two components and are read by the position sensing detector and the phase detector for further processing.

8. The sensor of claim 7, wherein a large non-linear deflection of the diffracted first order p-polarized beam reflected by the beam splitter is measured by a first position sensing device.

9. The sensor of claim 8, wherein the magnitude of deflection of the p-polarized probe beam is a function of the glucose concentration.

10. The sensor of claim 6, further comprising of:
a polarization mixing optical element.

11. the sensor of claim 10, wherein a beat signal is generated by mixing the s-polarized probe beam and the p-polarized probe beam.

12. The sensor of claim 1, wherein the first laser source beam is directed to and focused on the sample through the top surface of the total internal reflection element for thermally exciting the glycated hemoglobin molecule.

* * * * *